US009254132B2

(12) United States Patent
Crews et al.

(10) Patent No.: US 9,254,132 B2
(45) Date of Patent: Feb. 9, 2016

(54) ENDOSCOPIC PLICATION DEVICE AND METHOD

(71) Applicant: Boston Scientific Scimed, Inc., Maple Grove, MN (US)

(72) Inventors: Samuel Crews, Palo Alto, CA (US);
Brett Swope, San Francisco, CA (US);
David Cole, San Mateo, CA (US);
Andrew Smith, San Francisco, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/710,439

(22) Filed: Dec. 10, 2012

(65) Prior Publication Data
US 2013/0098967 A1 Apr. 25, 2013

Related U.S. Application Data

(63) Continuation of application No. 11/900,757, filed on Sep. 13, 2007, now abandoned, and a continuation-in-part of application No. 11/542,457, filed on Oct. 3, 2006.

(60) Provisional application No. 60/825,534, filed on Sep. 13, 2006, provisional application No. 60/723,160, filed on Oct. 3, 2005, provisional application No. 60/754,417, filed on Dec. 28, 2005, provisional application No. 60/825,534, filed on Sep. 13, 2006.

(51) Int. Cl.
*A61B 17/08* (2006.01)
*A61B 17/068* (2006.01)
*A61B 17/072* (2006.01)
*A61B 17/115* (2006.01)
*A61B 17/128* (2006.01)
*A61F 5/00* (2006.01)
*A61B 17/02* (2006.01)
*A61B 17/00* (2006.01)
*A61B 17/30* (2006.01)

(52) U.S. Cl.
CPC .............. *A61B 17/068* (2013.01); *A61B 17/072* (2013.01); *A61B 17/115* (2013.01); *A61B 17/1285* (2013.01); *A61F 5/0086* (2013.01); *A61B 17/0218* (2013.01); *A61B 17/07292* (2013.01); *A61B 2017/00535* (2013.01); *A61B 2017/00827* (2013.01); *A61B 2017/1157* (2013.01); *A61B 2017/306* (2013.01)

(58) Field of Classification Search
CPC ........... A61B 17/068; A61B 17/07292; A61B 17/1114; A61B 17/115; A61B 17/1155
USPC .......................................................... 606/219
See application file for complete search history.

(56) References Cited

U.S. PATENT DOCUMENTS 4,488,523 A * 12/1984 Shichman ................... 227/179.1
4,589,416 A *  5/1986 Green ........................... 606/220
(Continued)

Primary Examiner — Gregory Anderson
(74) Attorney, Agent, or Firm — Bookoff McAndrews, PLLC

(57) ABSTRACT

In a method of stapling layers of tissue within a body cavity, an engaging instrument is passed between a stapler cartridge and anvil and used to engage a region of tissue. The engaging instrument is retracted to move the engaged tissue into the stapling position, and driving staples from the cartridge through at least two layers of the engaged tissue. The method and associated system may be used to form plications in body tissue, such as stomach wall tissue. Staples simultaneously driven through tissue may simultaneously capture a reinforcing elements positioned adjacent the cartridge and/or anvil prior to stapling.

32 Claims, 19 Drawing Sheets

(56) References Cited

U.S. PATENT DOCUMENTS

| | | | |
|---|---|---|---|
| 4,848,367 A * | 7/1989 | Avant et al. | 128/898 |
| 5,263,629 A * | 11/1993 | Trumbull et al. | 227/181.1 |
| 5,271,543 A * | 12/1993 | Grant et al. | 227/179.1 |
| 6,126,058 A * | 10/2000 | Adams et al. | 227/180.1 |
| 6,503,257 B2 * | 1/2003 | Grant et al. | 606/151 |
| 7,220,237 B2 * | 5/2007 | Gannoe et al. | 604/8 |
| 7,744,627 B2 * | 6/2010 | Orban et al. | 606/215 |

* cited by examiner

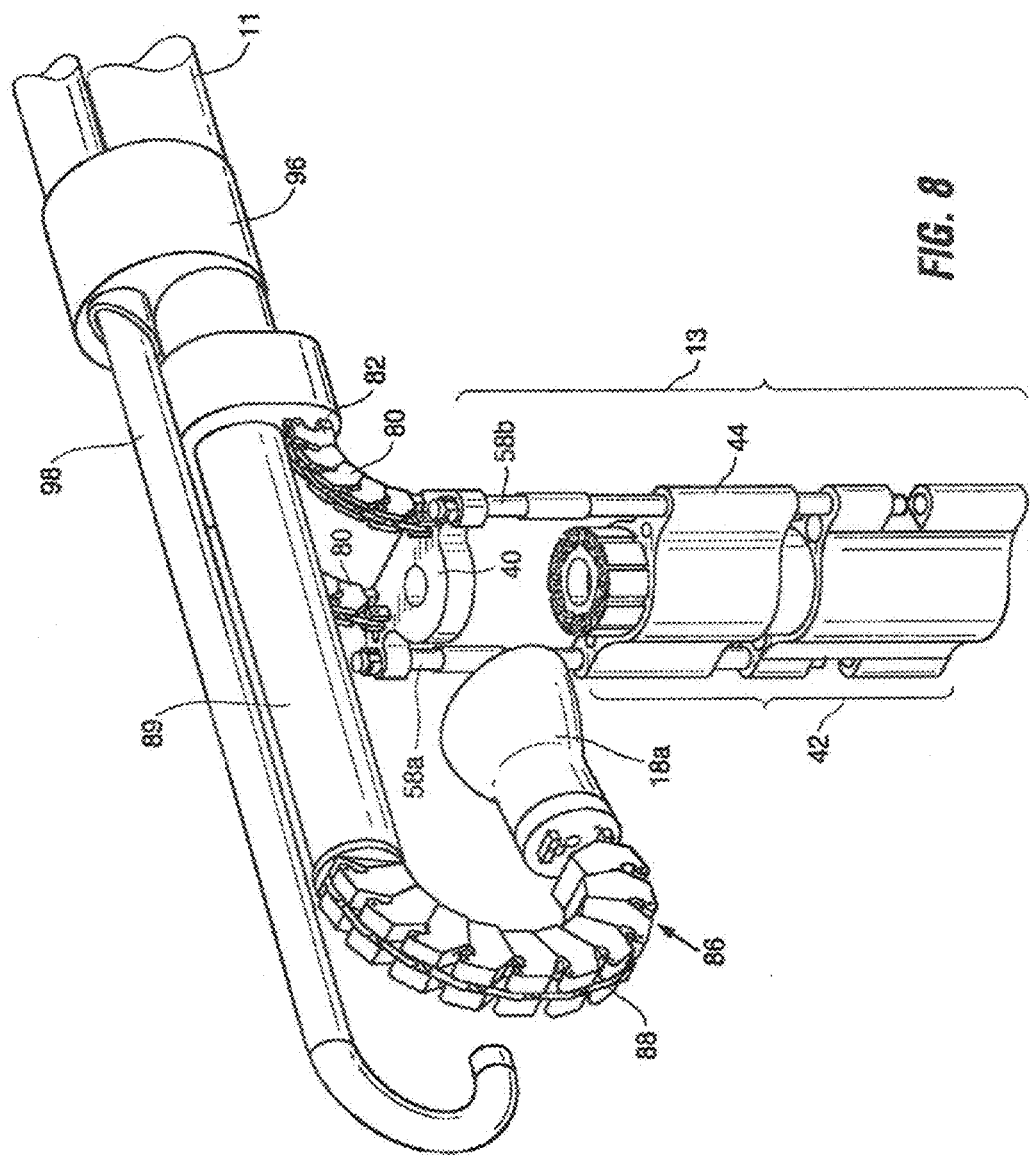

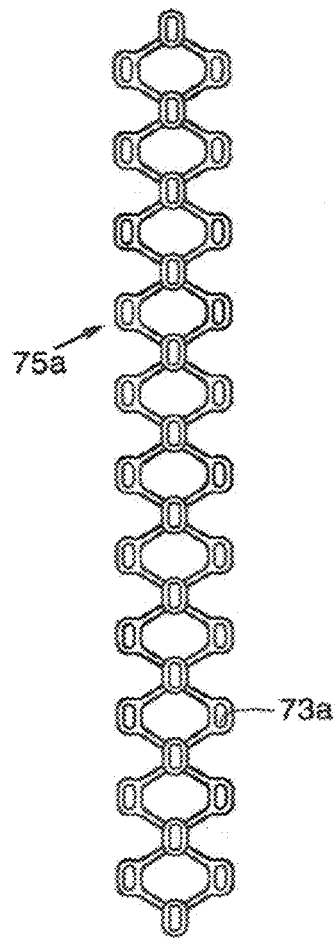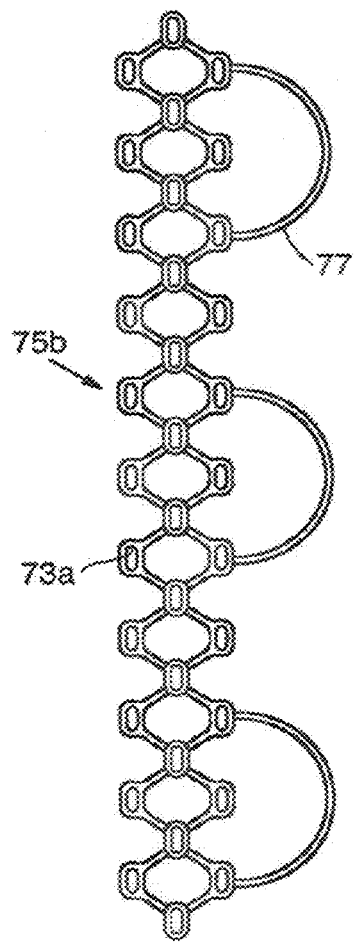
*FIG. 16A*     *FIG. 16B*
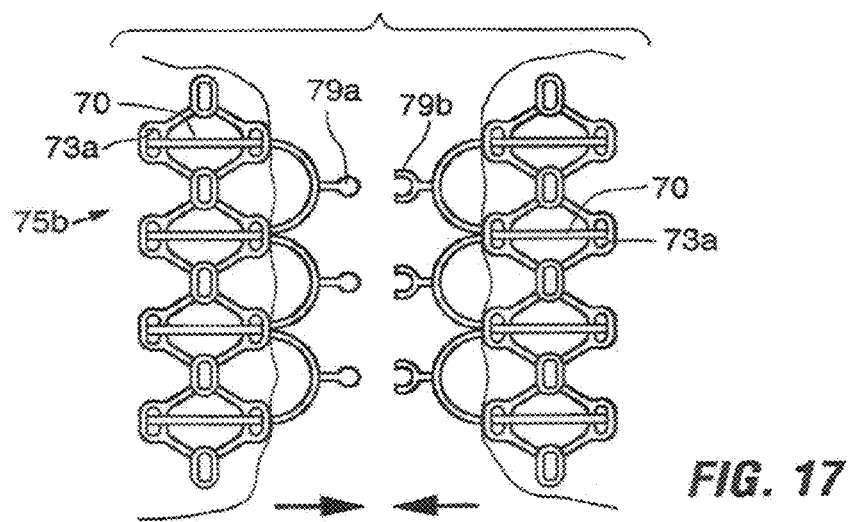
*FIG. 17*

ENDOSCOPIC PLICATION DEVICE AND METHOD

PRIORITY

This application is a continuation of U.S. Non-Provisional application Ser. No. 11/900,757, filed Sep. 13, 2007. Application Ser. No. 11/900,757 claims the benefit of U.S. Provisional Application No. 60/825,534, filed Sep. 13, 2006. Application Ser. No. 11/900,757 is also a continuation-in-part of U.S. application Ser. No. 11/1542,457, filed Oct. 3, 2006, which claims the benefit of U.S. Provisional Application No. 60/723,160, filed Oct. 3, 2005; U.S. Provisional Application No. 60/754,417, filed Dec. 28, 2005; and U.S. Provisional Application No. 60/825,534, filed Sep. 13, 2006.

FIELD

The present invention relates generally to the field of systems and methods for performing endoscopic surgery, and specifically to systems and methods for endoscopic plication of tissue within body cavities.

BACKGROUND

An anatomical view of a human stomach S and associated features is shown in FIG. 1A. The esophagus E delivers food from the mouth to the proximal portion of the stomach S. The z-line or gastro-esophageal junction Z is the irregularly-shaped border between the thin tissue of the esophagus and the thicker tissue of the stomach wall. The gastro-esophageal junction region G is the region encompassing the distal portion of the esophagus E, the z-line, and the proximal portion of the stomach S.

Stomach S includes a fundus F at its proximal end and an antrum A at its distal end. Antrum A feeds into the pylorus P which attaches to the duodenum D, the proximal region of the small intestine. Within the pylorus P is a sphincter that prevents backflow of food from the duodenum D into the stomach. The middle region of the small intestine, positioned distally of the duodenum D, is the jejunum J.

FIG. 1B illustrates the tissue layers forming the stomach wall. The outermost layer is the serosal layer or "serosa" S and the innermost layer, lining the stomach interior, is the mucosal layer or "mucosa" MUC. The submucosa SM and the multi-layer muscularis M lie between the mucosa and the serosa.

Prior applications, including WO 2005/037152 (incorporated herein by reference in its entirety) describe methods according to which medical implants are coupled to tissue structures formed within the stomach. According to these applications, devices for inducing weight loss (e.g. by restricting and/or obstructing flow of food into the stomach, and/or by occupying a portion of the stomach volume) may be coupled to tissue tunnels or plications P (FIG. 2) formed from stomach tissue.

For example, U.S. application Ser. No. 11/439,461, Filed May 23, 2006, (incorporated herein by reference in its entirety), describes a Restrictive and/Or Obstructive Implant System for Inducing Weight Loss. In one embodiment, flexible loops 2 (FIG. 3) are coupled to tissue plications P (FIG. 2) formed in the gastroesophageal junction region of the stomach. An implant, such as a flow restrictive and/or obstructive implant 4 (FIG. 4), is passed through the loops 2 and thus retained in the stomach as shown in FIG. 5.

U.S. application Ser. No. 11/542,457, filed Oct. 3, 2006 discloses other implants, including a restrictive pouch having anchors extending from its outer surface. During implantation, the anchors are inserted to cutouts/holes formed in plicated tissue.

In other instances, tissue plications may themselves be sufficient to provide the necessary treatment. For example, the plications may be used to reduce stomach volume or form a flow restriction within the stomach. Two or more plications may be drawn together and retained in some way, such as to form a restriction and/or reduce stomach volume, as also described in U.S. application Ser. No. 11/542,457, filed Oct. 3, 2006.

Other types of implants may be coupled to such plications or other tissue structures for a variety of purposes. These implants include, but are not limited to gastric space occupiers, prosthetic valves for the treatment of gastro-esophageal reflux disease, gastric stimulators, pH monitors and drug eluting devices that release drugs, biologies or cells into the stomach or elsewhere in the GI tract. Such drug eluting devices might include those which release leptin (a hormone which creates feelings of satiety), Ghrelin (a hormone which creates feelings of hunger), octreotide (which reduces Ghrelin levels and thus reduces hunger), Insulin, chemotherapeutic agents, natural biologics (e.g. growth factor, cytokines) which aid is post surgery trauma, ulcers, lacerations etc. Still other implants might be of a type which might provide a platform to which specific cell types can adhere, grow and provide biologically-active gene products to the GI tract, and/or a platform for radiation sources that can provide a local source of radiation for therapeutic purposes, or provide a platform whereby diagnostic ligands are immobilized and used to sample the GI tract for evidence of specific normal or pathological conditions, or provide an anchor point for imaging the GI tract via cameras and other image collecting devices.

Prior applications listed above address the desirability of forming tissue plications, pockets or tunnels in a way that regions of serosal tissue (i.e. the tissue on the exterior surface of the stomach) are retained in contact with one another. Over time, adhesions formed between the opposed serosal layers create strong bonds that can maintain the plication over extended durations, despite the forces imparted on them by abdominal movement and implanted devices. More durable plications can be created by placing any of a number of materials and/or substances (e.g. injectable sclerosing agents) between the serosal surfaces prior to plicating the serosal surfaces together. One example of material suitable for this purpose is polypropolyene mesh, commonly used for hernia repair, which when inserted in the plication fold provides a durable anchoring position within the GI tract.

Regardless of the application for which a plication is being formed, it is highly desirable to form that plication using steps carried out from within the stomach using instruments passed down the esophagus, rather than using more invasive surgical or laparoscopic methods.

The present application describes endoscopic plicators which may be passed transorally into the stomach and used to plicate stomach tissue by engaging tissue from inside of the stomach and drawing it inwardly. A section of stomach wall tissue drawn inwardly will be referred herein as a "pinch" of tissue, although it may be drawn inwardly using suction or other means. In preferred embodiments, a retracting component draws tissue into the path of travel of a stapler head. Vacuum and/or mechanical retractors may be used for retraction. By drawing a portion of the stomach wall between the stapler head and anvil, the retracting component causes sections of serosal tissue on the exterior of the stomach to be positioned facing one another. The disclosed plicators deliver staples to secure the opposed sections of tissue to one another, but instead may deliver sutures or other means for maintaining contact between the tissue sections at least until serosal bonds form between them. The plicator may pass a mesh element and/or sclerosing agent through the stomach wall into position between the opposed regions of serosal tissue thus enhancing serosal bonding. Each of these steps may be performed wholly from the inside of the stomach and thus can eliminate the need for any surgical or laparoscopic intervention. Medical devices may then be attached to the anchor for retention within the stomach.

While this application describes plication systems and methods with respect to the formation of plications is stomach tissue, the embodiments described herein have equal applicability for forming plications in parts of the body within or outside the GI system.

BRIEF DESCRIPTION OF THE DRAWINGS

FIG. 8 is a perspective view of a second embodiment of a plication system.

FIGS. 15A and 15B are plan views of a tissue plication, in which FIG. 15A shows the side of the plication positioned on the staple cartridge side of the plicator, and FIG. 15B shows the side of the plication position on the anvil side of the plicator.

FIGS. 16a and 16b are plan views showing staple reinforcements suitable for use with linear staple patterns.

FIG. 17 schematically illustrates the use of the staple reinforcements of FIG. 16b to support fasteners for engaging tissue plications to one another.

In FIG. 21C, the reinforcing element is shown being deployed from a hollow tube.

DETAILED DESCRIPTION OF THE DRAWINGS

Plication System

Figure 1A:
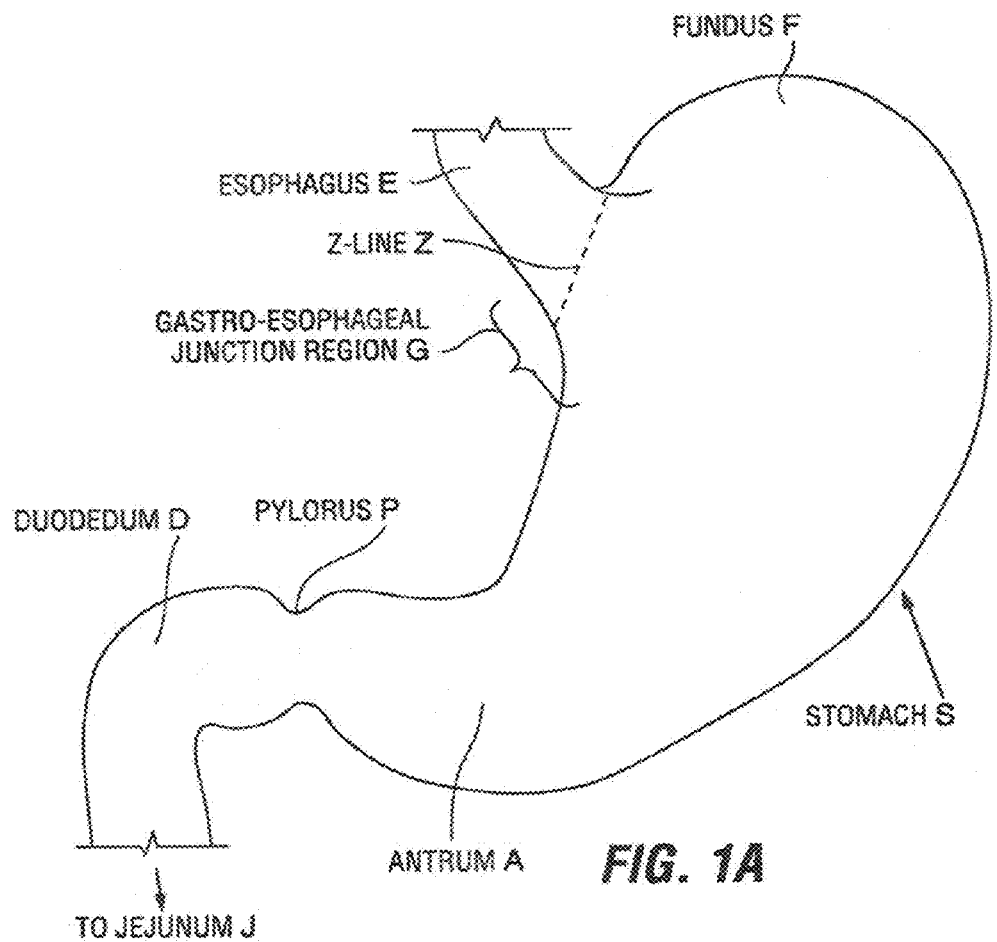
FIG. 1A is a schematic illustration of a human stomach and a portion of the small intestine.
Figure 1B:
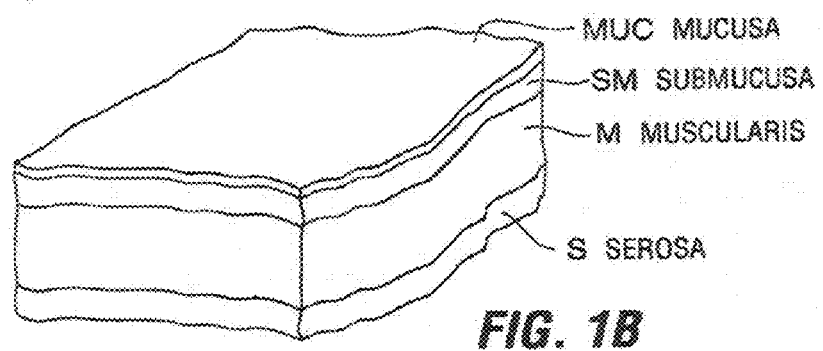
FIG. 1B is a cross-sectional perspective view of a portion of a stomach wall, illustrating the layers of tissue forming the wall.
Figure 2:
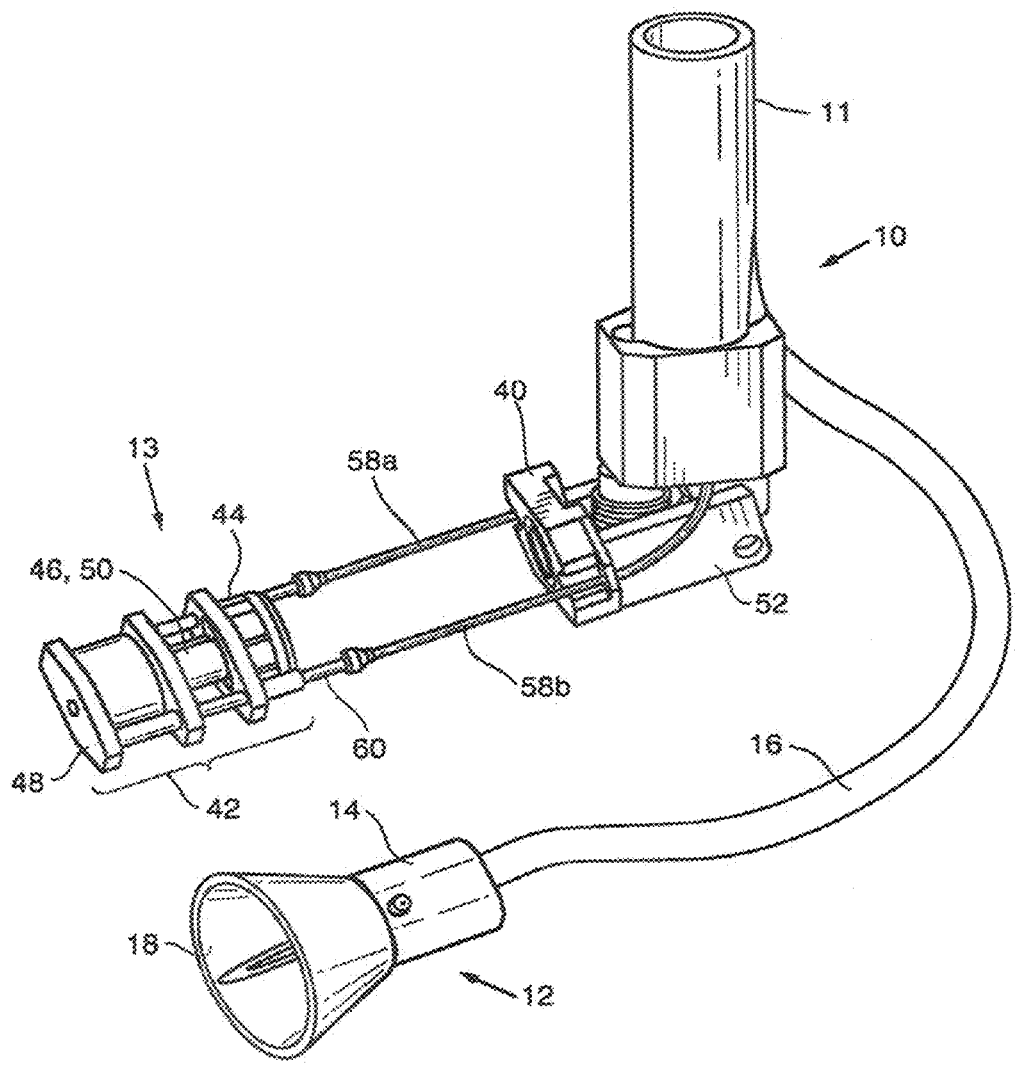
FIG. 2 is a perspective view of a plication system.
Figure 3:
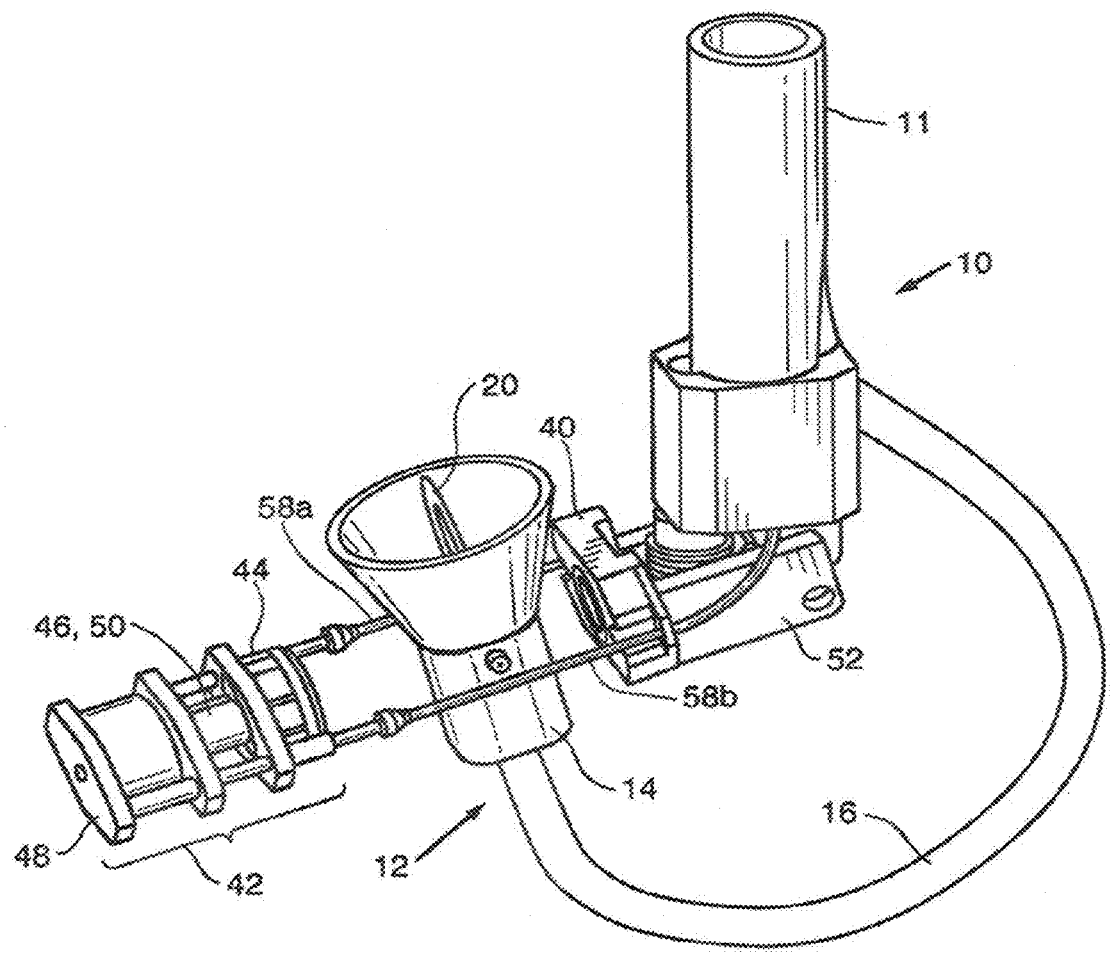
FIG. 3 is a perspective view of the system of FIG. 2 with the vacuum head in a tissue engaging position.

FIG. 2 illustrates one embodiment of a system 10 for tissue plication that is suitable for endoscopic use, as well as surgical or laparoscopic use if desired.

Generally speaking, system 10 includes a main shaft 11 having a distal portion extendable through the esophagus into the stomach. The distal portion of the main shaft 11 includes a retracting component 12 and a stapling component 13 comprised of an anvil 40 and a staple head 42. During use of the system 10, the retracting component 12 is used to engage stomach wall tissue and draw the tissue into a position between the anvil 40 and staple head 42, allowing staples to be driven through the stomach wall tissue to form a plication. By drawing a "pinch" of the stomach wall inwardly and then stapling the tissue, regions of serosal tissue are stapled to one another. Over time, these serosal tissue layers will adhere to form relatively strong bonds giving the plications sufficient durability to support implants within the stomach.

Retracting component 12 is provided with a vacuum head 14 and a flexible tube 16. Tube 16 preferably includes an insertion configuration in which it extends approximately longitudinally relative to the main shaft 11 for streamlined advancement of the tube 16 through the esophagus. Tube 16 is equipped with pull-wires (not shown) and/or alternative means for articulating or retroflexing the vacuum head 14 as needed for proper positioning within the stomach.

Vacuum head 14 defines a vacuum chamber 18 having an opening that, during use, is positioned into contact with stomach tissue so as to draw the tissue into the chamber 18. Vacuum chamber is preferably formed of a flexible material such as silicone, urethane or other suitable materials. Tube 16 is fluidly coupled to a source of negative pressure such as a syringe or vacuum pump such that application of suction to the tube 16 creates a vacuum in the vacuum chamber.

A hollow needle 20 is advanceable through the tube 16 into the vacuum chamber 18. Hollow needle 20 includes a pointed distal tip sufficiently sharp to penetrate stomach wall tissue (FIGS. 7A-7B) when advanced against tissue drawn into the vacuum chamber. An optional tissue engaging element (not shown in FIGS. 2-6) is positioned within the hollow needle 20. As shown in FIGS. 7C-7E, the tissue engaging element is deployable from the hollow needle 20 and placed in an expanded state after the needle 20 has been advanced through tissue, and it is then withdrawn proximally using an attached tether or catheter following deployment to maintain engagement with the tissue.

Various types of engaging elements may be used for this purpose. In the embodiment shown in FIG. 7D, the engaging element 22a may be a balloon 24 mounted on a small diameter catheter 26 extendable through the needle 20. After the balloon 24 is expanded on the serosal side of the stomach wall, tension is applied to the catheter 26 as shown in FIG. 7E to hold the retracted tissue between the anvil 40 and staple head 42 (not shown in FIGS. 7A-7E but discussed below) for stapling. The vacuum chamber 18 may be withdrawn from the tissue to move it out of the area between the staple cartridge and anvil. Staples are then driven through the tissue in the direction of arrow A. The balloon may be removed after stapling or it may be left in place within the body. If the balloon is to be left in the body, it may be formed of a biodegradable or bioerodible material, or a more permanent biocompatible material.

As mentioned previously, stapling component 13 includes an anvil 40 and a stapler head 42. Although FIGS. 2-6 show the head 42 positioned distally of the anvil 40, in other embodiments the positions of these features might be reversed. Likewise, while in the illustrated embodiments the staple head is advanced to compress the tissue, in other embodiments the anvil might instead be advanced.

Figure 5:
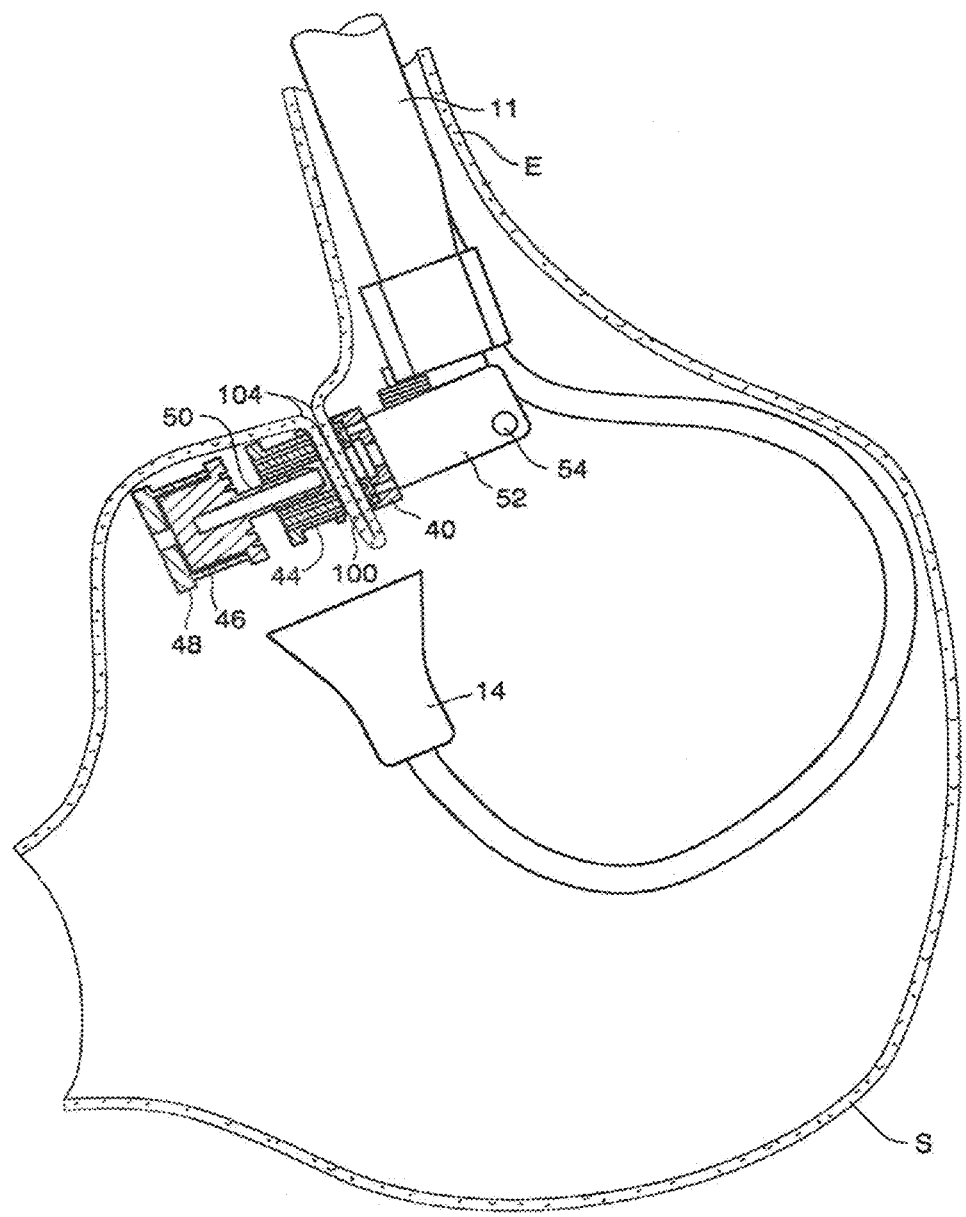
FIG. 5 is a cross-section view similar to the view of FIG. 4.
Figure 6:
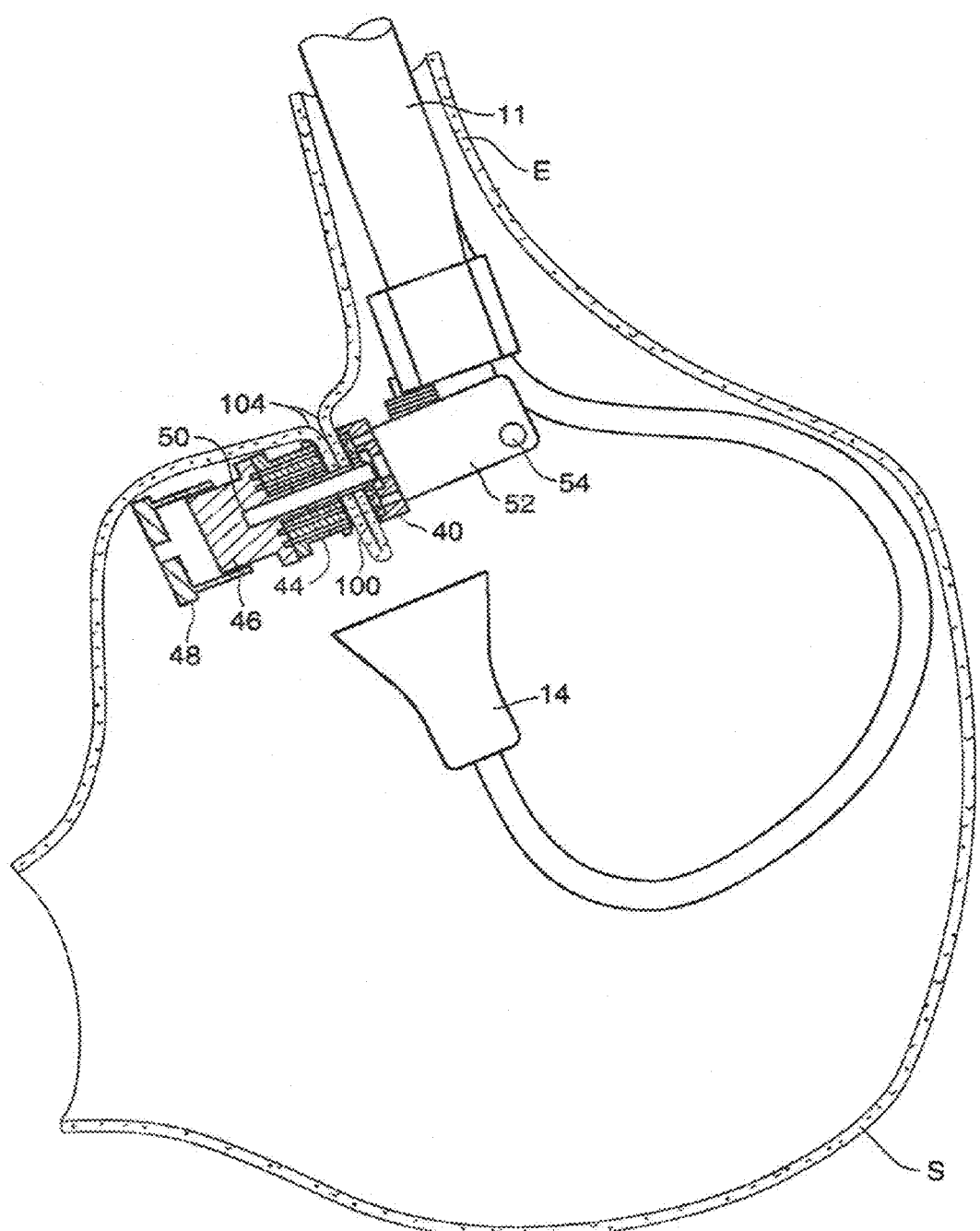
FIG. 6 is similar to FIG. 5 and shows activation of the staple driver to fire staples from the cartridge.

The stapling component 13 is pivotable relative to the main shaft 11 so that once the stapling component 13 is positioned within the stomach, it may be moved laterally towards the stomach wall. In the FIG. 2 embodiment, anvil 40 is mounted to an articulated base 52 coupled to the main shall 11 at pivot point 54 (FIG. 5), allowing for rotation of the base (and thus the stapling component 13) relative to the main shaft 11. The base 52 is moveable to a longitudinal position (not shown) relative to the shaft to facilitate streamlined movement of the system 10 through the esophagus. As shown in FIG. 5, a motor driven worm screw 56 is activated to articulate the base 52.

Figure 4:
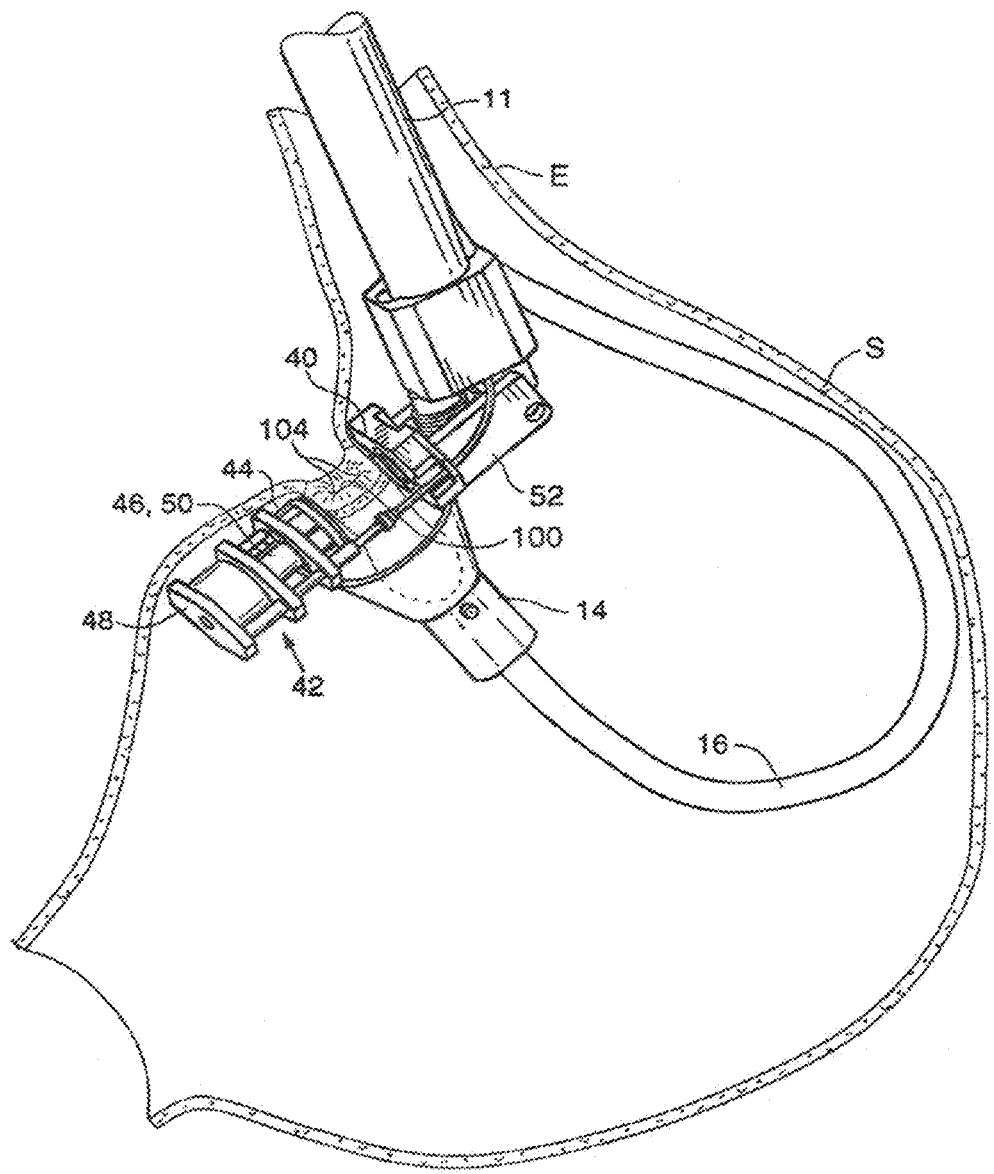
FIG. 4 is a perspective view of the system of FIG. 3, showing tissue being engaged by the vacuum head and compressed by the system.

As best shown in FIG. 5, staple head 42 includes a staple cartridge 44 containing staples (not visible in the drawing), and a staple driver 46 positioned to drive staples from the cartridge 44 when it is advanced proximally into contact with the staples. Fluid lines 58a, 58b extend from the cartridge 44 and staple driver 46 respectively and are coupled to air, gas or other fluid (any of which will be referred to as "fluid") sources positioned external to the body. During use, fluid or gas pressure is directed through fluid line 58a and used to advance the staple cartridge 44 into contact with tissue positioned between the anvil 40 and cartridge 44 as shown in FIG. 4, thereby compressing the tissue. In an alternative embodiment, the fluid line 58a may be replaced with a cable configured to drive a lead screw that, when activated, advances the staple cartridge 44 to compress tissue disposed within the gap between the anvil 40 and the staple cartridge 44.

Once tissue is compressed between the cartridge 44 and anvil 40, fluid/gas is then directed through fluid line 58b to pressurize cylinder 48 sufficiently to drive the staple driver 46 into contact with staples positioned in the staple cartridge 44. A tissue cutting element 50, which in the illustrated embodiment is a tubular element having a sharpened end, is coupled to the staple driver 46 such that it will core through the tissue during stapling to form a hole in the plication.

Figure 23A:
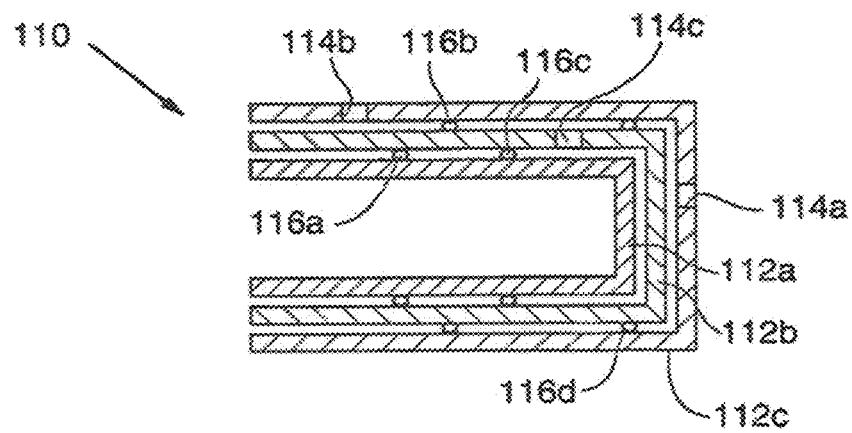
FIGS. 23A and 23B are cross-section views illustrating hydraulic systems that may be used for tissue compression and staple driving in the system of FIG. 2.
Figure 23B:
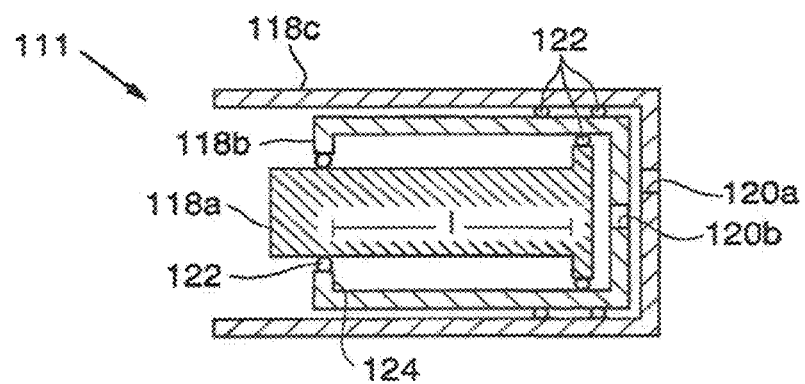

FIGS. 23A and 23B show collapsible hydraulic systems that may be used to advance the cartridge 44 and staple driver 46.

System 110 of FIG. 23A allows for sequential movement of the cartridge and the driver allowing for compression and then stapling. System 110 includes nested cylinders 112a, 112b and 112c, fluid inlets 114a, 114b and 114c, and o-ring seals 116a-d. When fluid pressure is introduced into the system via inlet 114a, cylinder 112b advances to the left. Once seal 116b of cylinder 112b crosses over inlet 114b, fluid pressure is applied to cylinder 112a through inlet 114c, causing cylinder 112a to begin moving towards the left of the drawing. This arrangement can be used to first compress (e.g. using staple cartridge coupled to cylinder 112b), and to then staple (e.g. using a staple driver coupled to cylinder 112a) the tissue using a single source of fluid or gas pressure.

System 111 of FIG. 23B is a telescoping fluid power actuator that may be used when the length of the path of travel needed for a feature (e.g. the stapler driver, cartridge, and/or anvil) would require a cylinder that is longer than can be accommodated by the environment (e.g the stomach). System 111 includes cylinders 118a, 118b and 118c, inlets 120a and 120b, and seals 122. Pressure applied at inlet 120a will cause cylinder 118a (which may be coupled to the cartridge) to advance to the left. Once cylinder 118a has moved a distance "l", it will engage with a shoulder 124 on cylinder 118b, causing cylinder 118b to travel with cylinder 118a as cylinder 118a continues to move. In this arrangement, a long stroke for cylinder 118a is gained from a short fluid power system.

FIG. 8 shows an alternative embodiment of a modified plication system 10a which utilizes rigidizable cables 80 to deflect the stapling component 13 relative to the main shaft 11. Cables 80 are preferably formed of a plurality of spine elements 82 strung onto a pull wire (not shown). Fluid lines 58a, 58b may extend through holes in the spine elements, or they may be separate from the cables 80. When tension is applied to the cables using actuators positioned outside the body, the spine elements 82 engage one other to stiffen the cable. The spine elements 82 may be shaped such that the cable will assume a predetermined bend when tension is applied to them.

In the FIG. 8 embodiment, a rigidizable cable 86 also carries the vacuum chamber 18a. Cable 86 includes a pull wire (not shown) extending through spine elements 88. The spine elements 88 are shaped to orient the chamber 18a for advancement between the anvil 40 and cartridge 44. Cable 86 may extend from a sheath 89 that is longitudinally extendable from a lumen in the main shaft 11.

Figure 10A:
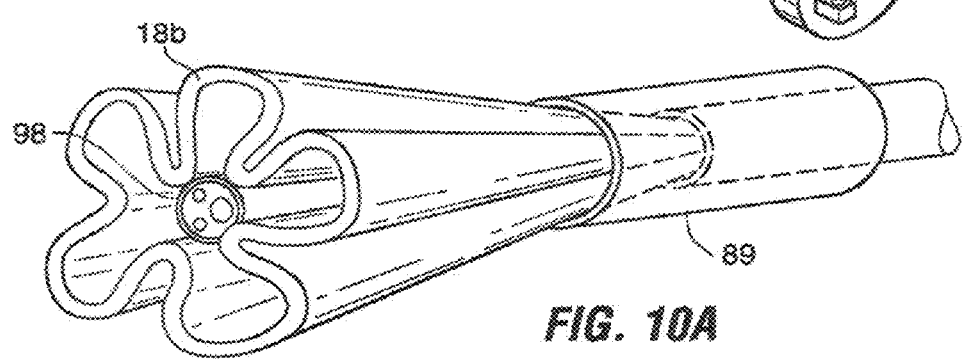
FIG. 10A is a perspective view of an embodiment of an expandable vacuum chamber, shown in the compressed position.
Figure 10B:
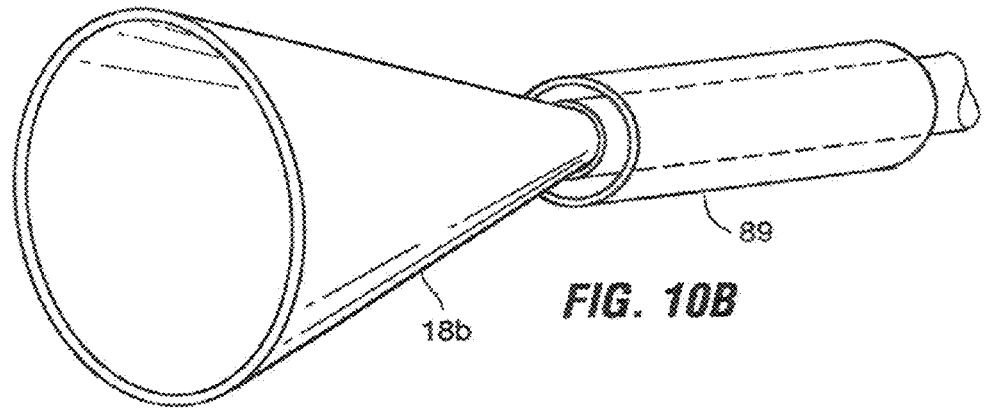
FIG. 10B is a perspective view of the vacuum chamber of FIG. 10A is the expanded position.

Vacuum chamber 18a may be foldable or compressible for positioning within the sheath 89. FIG. 10A shows a folded vacuum chamber 18b beginning to expand as it exits the distal end of sheath 89, and FIG. 10B shows the vacuum chamber 18b fully expanded after exiting the sheath 89. FIG. 10A illustrates that in alternative embodiments, endoscopes 98 and/or other instruments may be passed through the vacuum chamber 18b to give access and/or visualization to the stomach wall or other organs or tissues. In the FIG. 8 embodiment, a collar 96 is positioned on the main shaft 11 for receiving endoscope 98.

Figure 9:
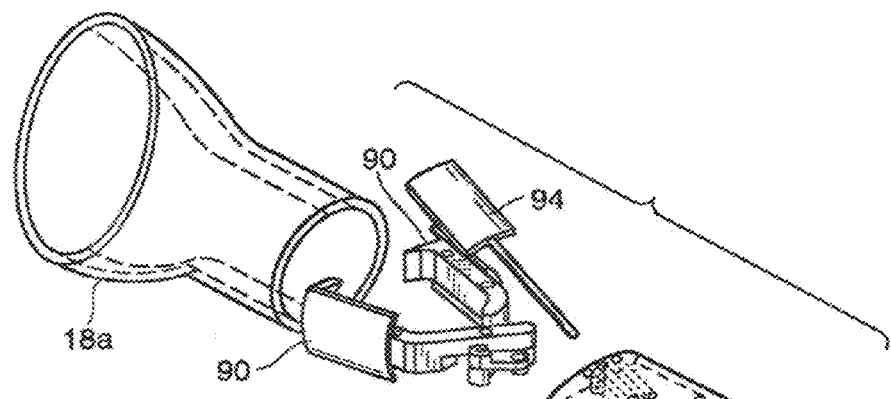
FIG. 9 is an exploded view of the retracting component of the embodiment of FIG. 8.

FIG. 9 is an exploded view of the vacuum chamber 18a of the FIG. 8 embodiment, and illustrates that a pair of gripping jaws 90 is positioned within the vacuum chamber 18a. The jaws 90 are constructed using a linkage arrangement and are controlled using a pull wire extending through a back plate 92 of the vacuum chamber 18a, through spine elements 88 (FIG. 8), and to the proximal end of the plicating system outside the body. Before vacuum is applied, the jaws are moved to an open position. When vacuum pressure draws tissue into the vacuum chamber 18a, the jaws 90 are closed to engage the tissue.

The FIG. 8/9 vacuum chamber 18a additionally includes stabilizing arms 94 extending into the vacuum chamber 18a. The stabilizing arms are retained in contact with the interior walls of the chamber 18a to prevent the chamber from collapsing when vacuum is applied. The arms may be moveable between closed and opened positions to allow the vacuum chamber to collapse for passage through the esophagus, or they may remain fixed in the opened position.

Plication Reinforcements

Reinforcements of various types may be implanted in or on plications formed using the plication system. Such reinforcements may function to reinforce the staple array, help to more evenly distribute the forces applied to the tissue by the staples, and/or facilitate bonding between the opposed serosal layer. Suitable reinforcements include ones positionable on or between the serosal tissue layers ("serosal side reinforcements"), as well as those delivered on the side of the mucosal tissue ("mucosal side reinforcements").

Figure 18A:
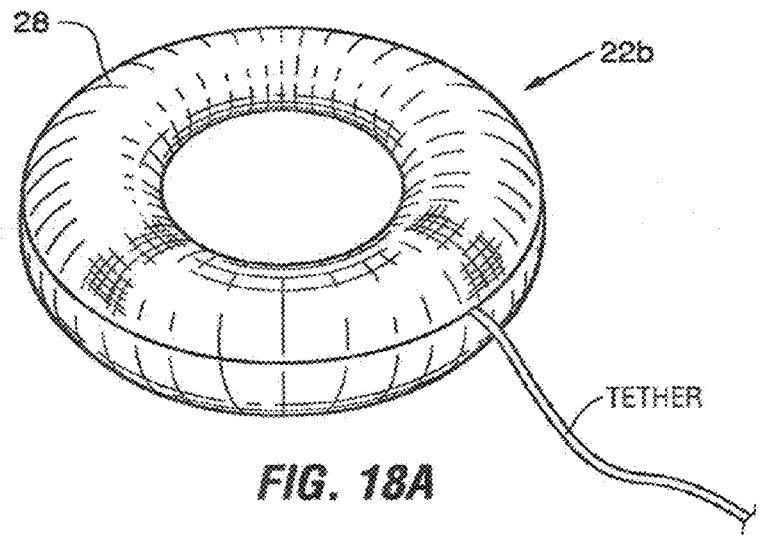
FIG. 18A illustrates an alternative engaging element.
Figure 18B:
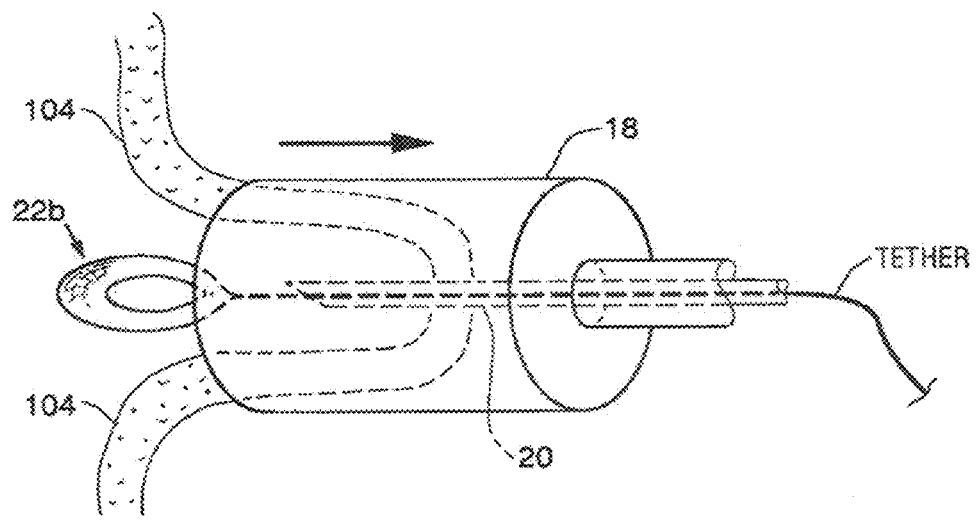
FIGS. 18B through 18E illustrate the sequence of steps for deploying the engaging element of FIG. 18A and retaining the engaging element within a tissue plication.
Figure 18C:
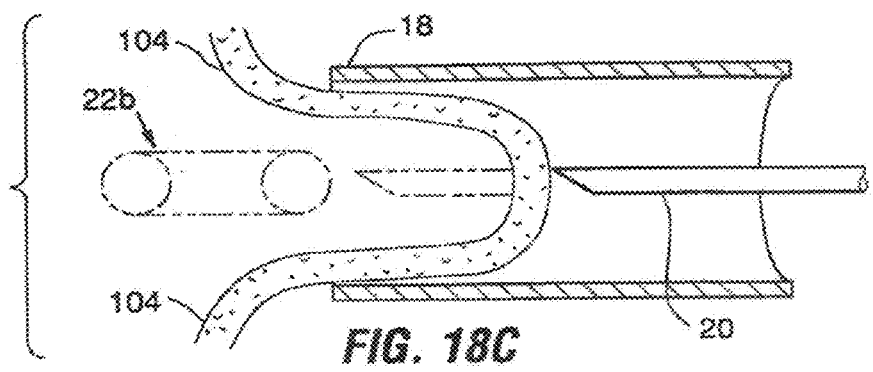
Figure 18D:
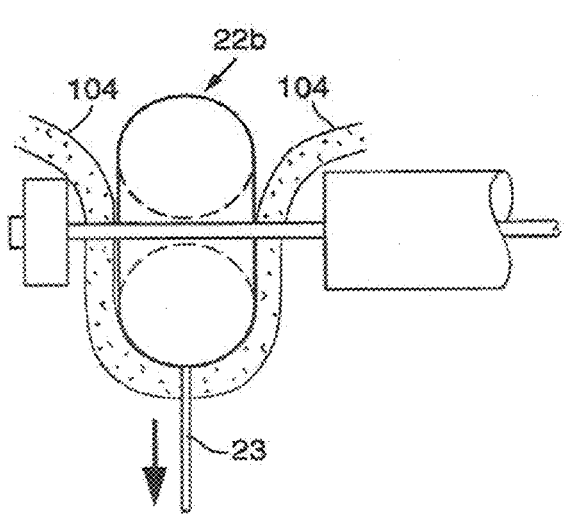
Figure 18E:
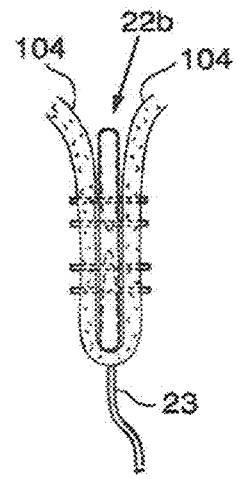

For serosal side reinforcements, a reinforcement similar to engaging element 22a described in connection with FIG. 7D may serve as a permanent or semi-permanent implant that will reinforce the staple array applied to the tissue and/or facilitate serosal tissue bonding between the layers of stomach wall tissue that are to be stapled together. For this purpose, the material may be a synthetic or non-synthetic mesh (formed of nitinol, polyester, or other natural or synthetic material), porous or non-porous material, slotted material or any other material through which adhesions will form or onto which tissue will grow. Examples include, but are not limited to, polypropylene, materials sold under the trade names Goretex or Dacron, or tissue graft material such as the Surgisis material sold by Wilson Cook Medical, Inc. The material may be treated with tissue-ingrowth promoting substances such as biologics. In an embodiment shown in FIG. 18A, the reinforcement 22b is a mesh/braid embedded in or coated with a dissolvable or bioabsorbable coating. The reinforcement 22b is preferably positioned in a manner similar to that described in connection with the balloon of FIG. 7D. Specifically, vacuum chamber 18 is used to engage a region of tissue where a plication is to be formed. Hollow needle 20 is advanced from within the chamber 18 through the stomach wall, and the reinforcement 22b is advanced from the hollow needle and inflated to a toroidal shape between the opposed regions 104 of serosal tissue. The reinforcement 22b may optionally be used for retraction of the stomach wall via application of tension on the tether 33 as shown in FIG. 18D. Staples driven through the tissue pierce and deflate the inflated reinforcement as shown in FIGS. 18D and 18E, and capture the deflated reinforcement between the opposed serosal tissue layers. The reinforcement is left in place between the two layers of stomach wall tissue after stapling. The coating on the deflated balloon dissolves, exposing the interstices of the underlying mesh or porous material to serosal growth.

Figure 19:
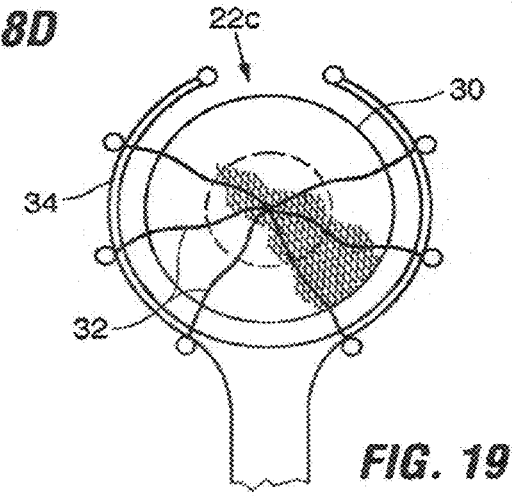
FIG. 19 illustrates an alternative engaging element and deployment hoop.

As shown in FIG. 19, the reinforcement 22c may instead be a mesh disk 30 detachably carried (e.g. using sutures 32) on a wire hoop 34 extendable through needle 20 in a compressed shape and then self-expandable to the illustrated position to expand the mesh, on the outside of the stomach. The sutures 32 are severed during stapling, leaving the mesh in place between the plicated tissue layers. The hoop 34 is withdrawn into the needle 20 and removed from the body.

Figure 20A:
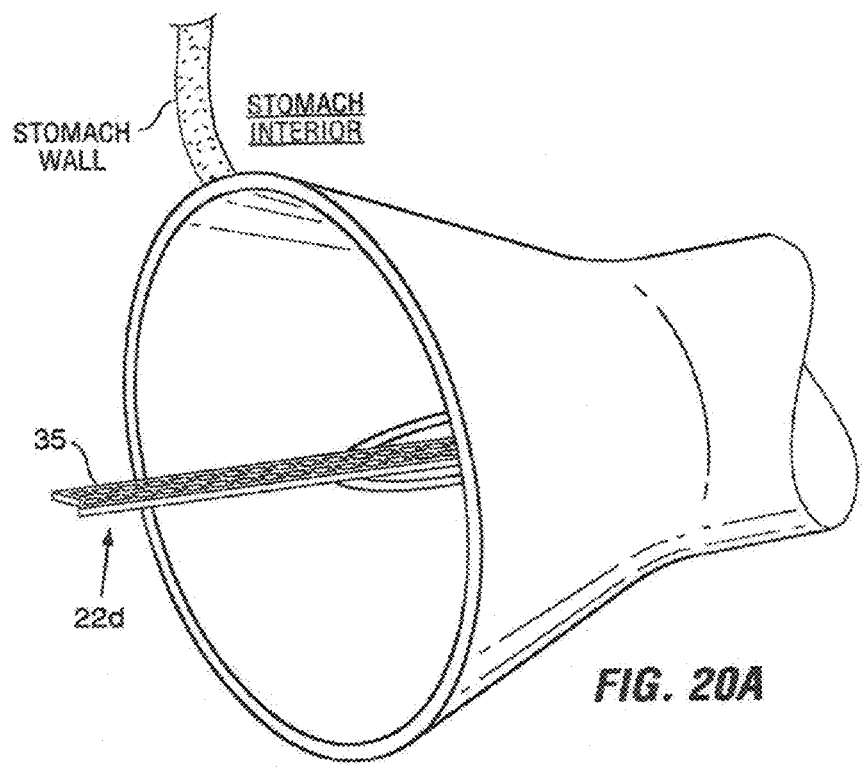
FIGS. 20A and 20B illustrate yet another engaging element being deployed from the hollow needle of the vacuum head.
Figure 20B:
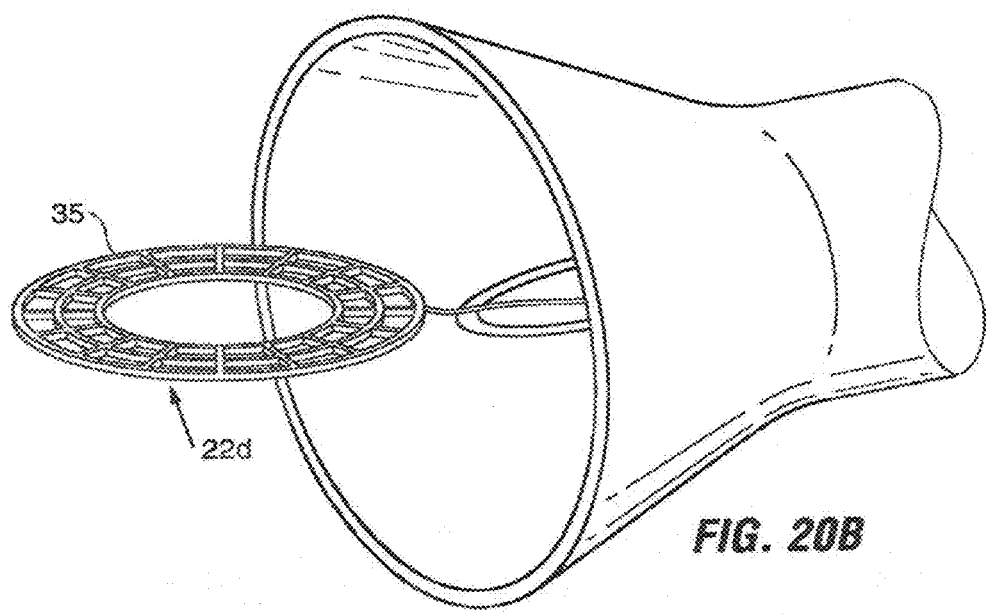

In another embodiment shown in FIGS. 20A and 20B, the reinforcement 22d may be an elongate nitinol mesh or braid backbone 35 that may be positioned longitudinally within the hollow needle 20, but that is shape set to assume a circular or other suitable configuration once released from the hollow needed between the serosal tissue layers. In modifications to this concept shown in FIGS. 21A-21C, the reinforcement 22e may be a wire 37 or ribbon shape set to assume one of a variety of expanded configurations when it is pushed out of the hollow needle 20. In the expanded configuration, the wire may assume a pattern shaped such that when it is positioned between serosal tissue layers, it will be captured by staples advanced through the tissue. As with the other reinforcements disclosed above, the pattern may be annular as in FIG. 21A or 21C, or it may be disk-like as in FIG. 21B. Moreover, while the patterns are shown to have an approximately circular silhouette, other shapes may instead be used.

Figure 22A:
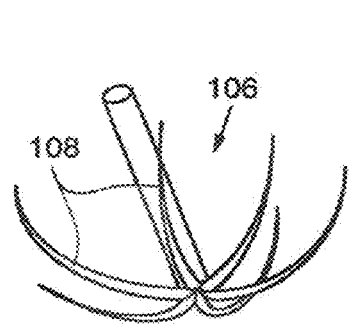
FIG. 22A is a perspective view of an expandable frame for deploying a reinforcing element.
Figure 22B:
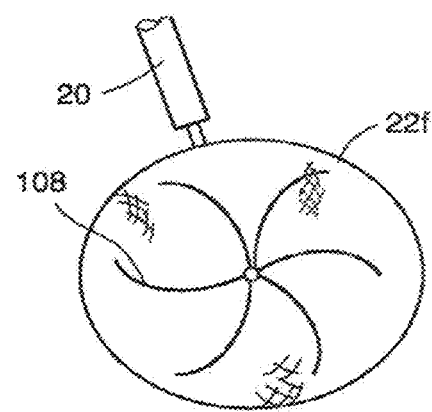
FIG. 22B shows a reinforcing element on the frame of FIG. 22A.

In another embodiment shown in FIGS. 22A and 22C, a reinforcement 22f (which may be formed of a polyester fabric or other material including those listed elsewhere in this application) is carried by a frame 106 having a plurality of outwardly extending arms 108 that spring to an expanded position when released from hollow tube 20. The reinforcement 22e is deployed using hollow needle 20 in a manner similar to those described above. Specifically, the hollow needle 20 is pierced through engaged stomach wall tissue, and the frame is advanced out the distal end of the needle 20 to allow arms 108 to spread to the expanded position shown in FIGS. 22A and 22C, thereby expanding the reinforcement 22e between the opposed serosal layers. The element is fixed between the layers by the staples driven through the opposed regions of stomach wall, and the frame is withdrawn from the needle and out of the body.

Mucosal side reinforcements may take the form of reinforcements that are positioned on or adjacent to one or both of the mucosal surfaces lining the "pinch" of tissue that will form the plication. These reinforcements may be features of the staples or staple arrays, or they may be separate components engaged by staples as the staples are advanced through the tissue.

Figure 11A:
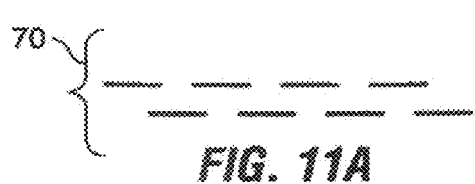
FIGS. 11A and 11B are plan views illustrating staple patterns.
Figure 11B:
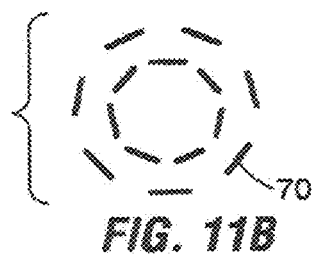
Figure 12A:
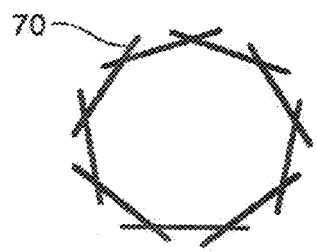
FIGS. 12A-12C an plan views illustrating interlocking staple patterns.
Figure 12B:
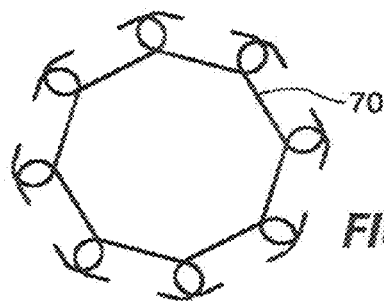
Figure 12C:
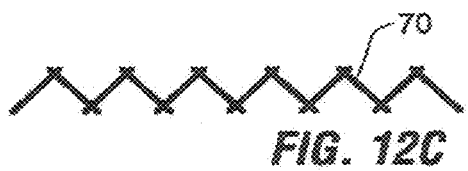
Figure 21A:
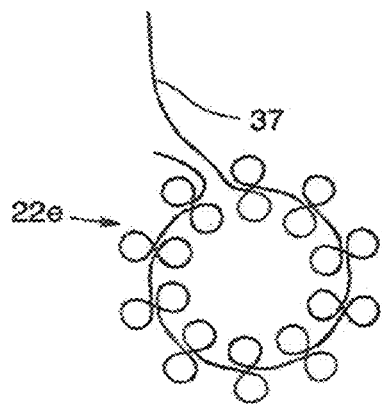
FIGS. 21A, 21B and 21C illustrate alternative reinforcing elements.
Figure 21B:
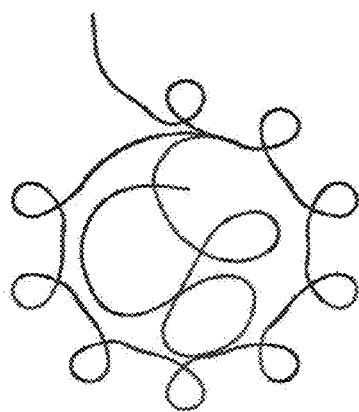
Figure 21C:
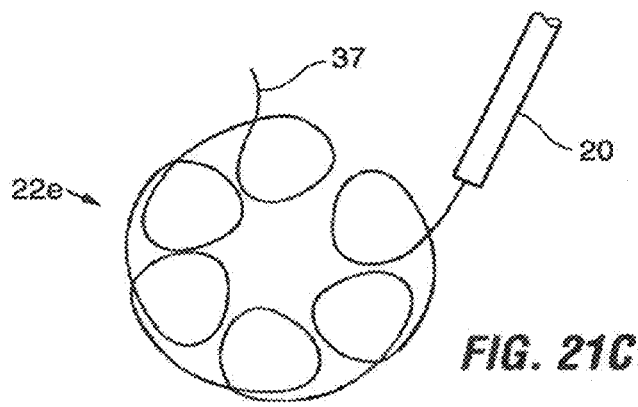

Referring to FIG. 21A, conventional stapling procedures will often include two parallel rows of staples, in which the staples in one row are laterally offset from the staples of the other row. According to the disclosed method, it is useful to employ this technique to the circular staple pattern delivered using the plicator 10, to produce two concentric rings of offset staples, as shown in FIG. 11B. It has been found to be additionally beneficial to form mucosal side reinforcements by linking or interlocking the staples to provide greater structural reinforcement to the stapled tissue and/or to more evenly distribute forces applied to the tissue by the staples. Linked staple arrays may be formed by arranging the staples 70 in the cartridge of the plicator 10 in a single circular pattern to interlock as shown in FIG. 12A, or in a double circular pattern with two concentric rings of interlocked staples. The staples 70a may be curvilinear so as to form a locking pattern shown in perspective view of FIG. 12B. A linear arrangement of staples 70 may also be linked as shown in FIG. 12C.

In alternative embodiments, staples are linked together by reinforcing members formed of metallic or polymeric materials, such as nitinol, titanium, stainless steel PEEK, or other biocompatible materials. According to these embodiments, the reinforcing members are positioned on one or both of the mucosal sides of the "pinch" of tissue engaged by the plication system such that they are captured by staples being driven through the tissue. In a preferred embodiment, the staples capture a cartridge side reinforcing ring 72 (FIG. 13A) as they leave the cartridge and/or capture an anvil side reinforcing ring 74 (FIG. 13B) as the anvil shapes and bends them. Upon completion of the plication, the staples are linked to one another so that they cannot separate or expand radially. The use of the reinforcing rings is advantageous compared with prior art staple buttressing materials such as sheets formed of bovine pericardium or hydrogel, both of which are penetrated (and thus potentially compromised) by staples as they are driven through the tissue. The open structure or lattice pattern of the reinforcing rings provides openings for the staples to pass through as well as supportive members for the staples to wrap around—so that the staples capture but do not penetrate the ring material. Over time, tissue may grow into the lattice structure and/or around the supportive members. The proportions of the ring, such as the sizes of the openings in the lattice structure, may be adjusted to increase or decrease the amount of ingrowth that might occur.

Figure 14A:
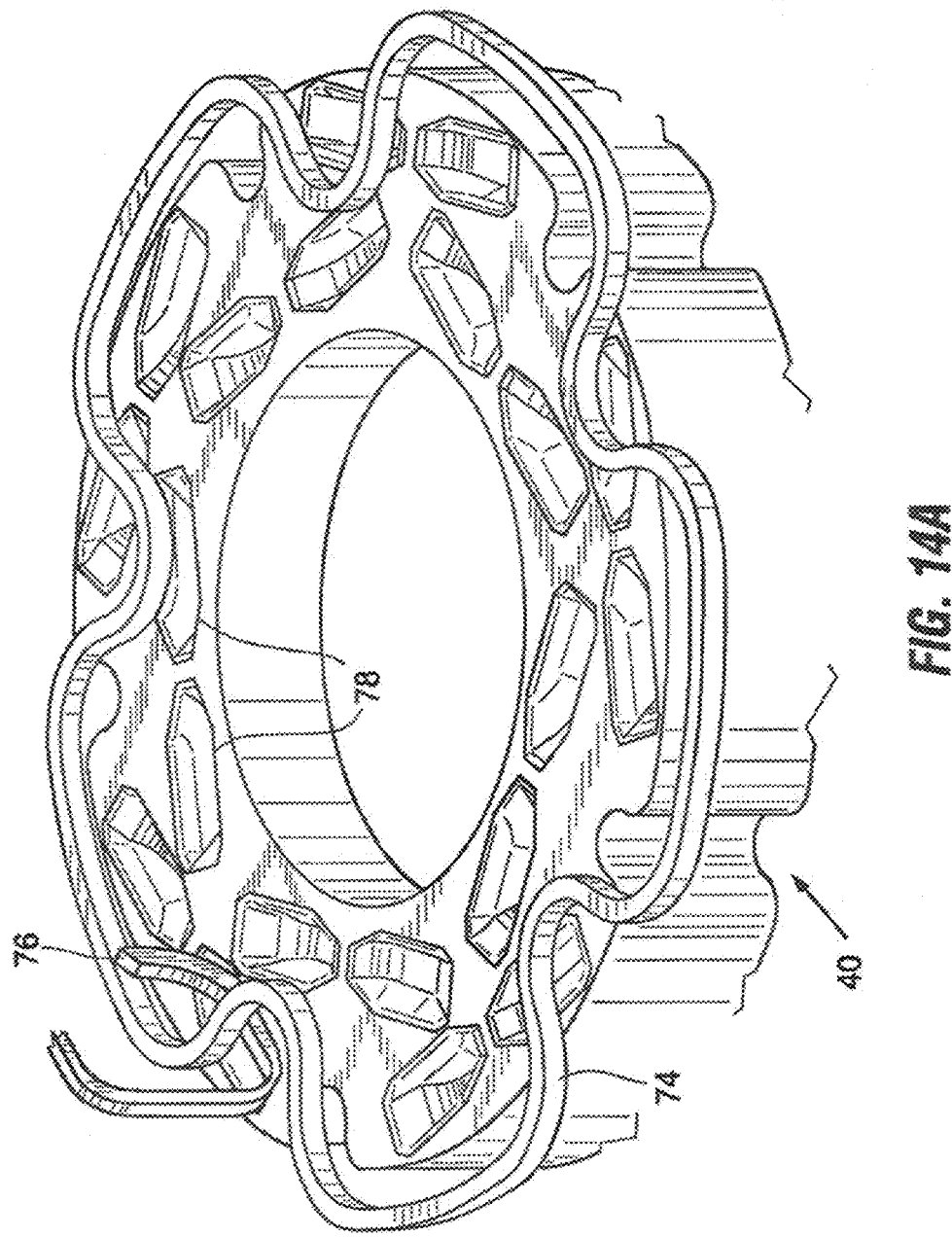
FIG. 14A is a perspective view showing the reinforcing ring of FIG. 13B on a stapler anvil.
Figure 14B:
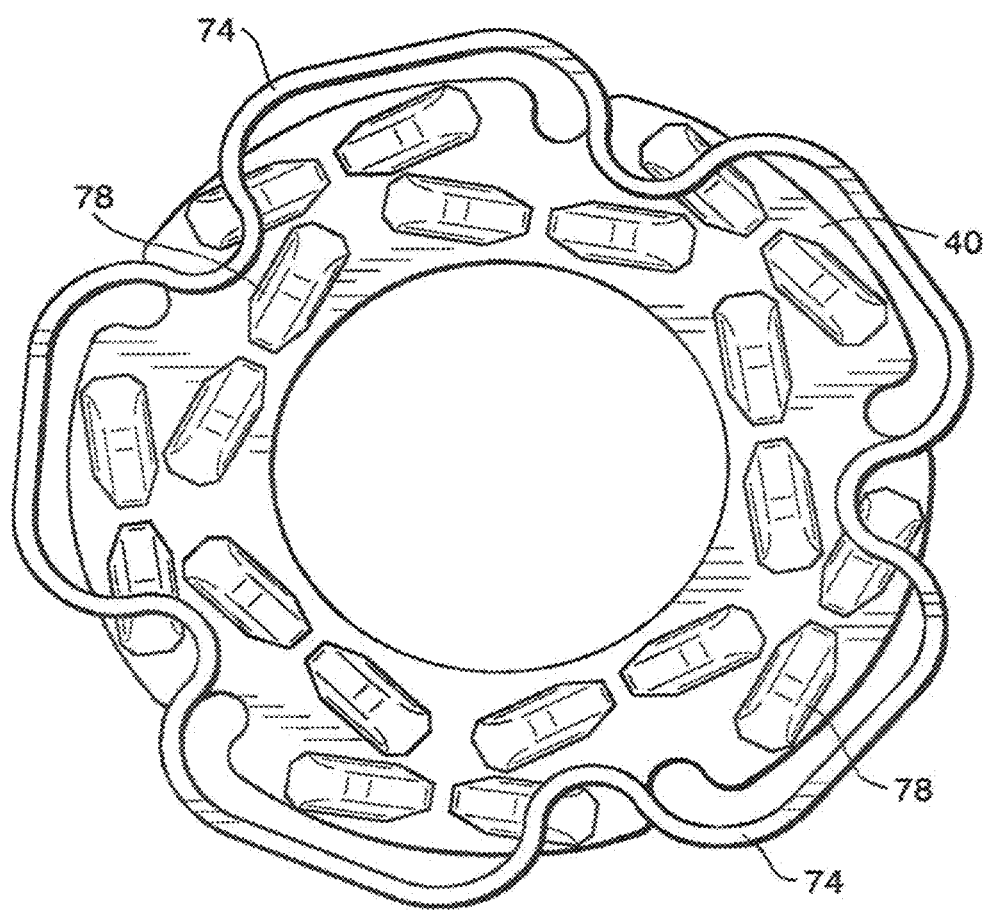
FIG. 14B is a plan view of the reinforcing ring and anvil of FIG. 14A.
Figure 14C:
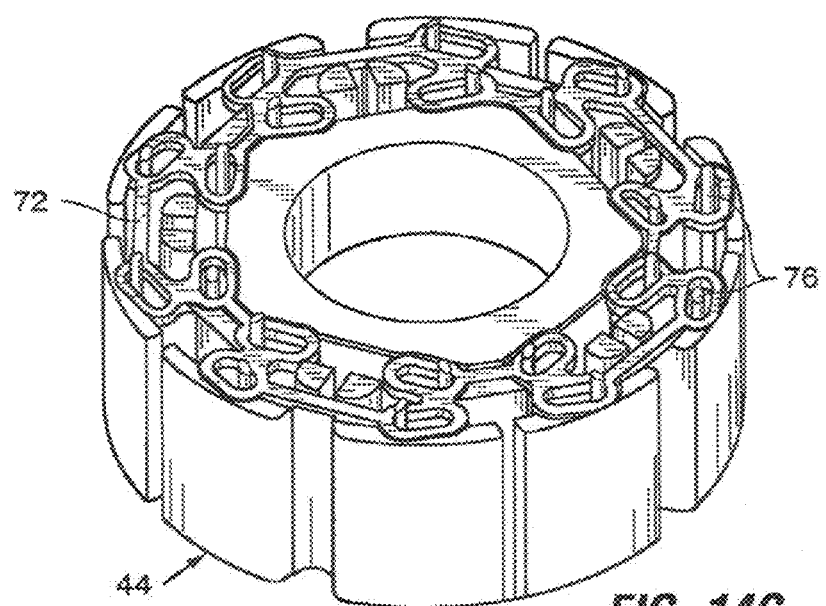
FIG. 14C is a perspective view showing the reinforcing ring of FIG. 13A on a staple cartridge.

The reinforcing rings are preferably provided separate from the staples although they instead may be integral with the staples. In this embodiment, ring 74 is positioned against the staple anvil 40 as shown in FIGS. 14A and 14B. The anvil may include retaining elements to maintaining the ring's position on the anvil. Ring 72 is seated within the cartridge 44, with the staples 70 aligned with their prongs 76 extending through openings 73 in the ring 72. Alternatively, the cartridge may have retaining elements to hold the ring in place prior to stapling.

Figure 15A:
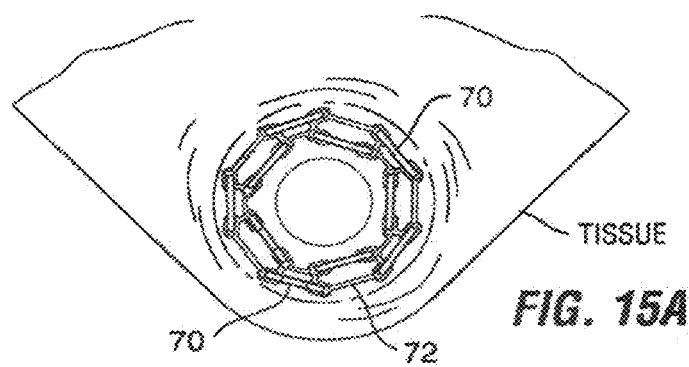
Figure 15B:
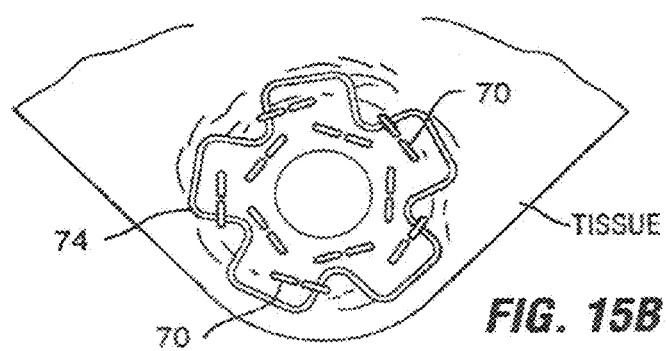

When staples 70 are driven from the cartridge, they advance further through openings 73, capturing ring 72 against the adjacent mucosal tissue as shown in FIG. 15A. The staple legs/prongs 76 pass through the stomach wall tissue into contact with the indentations 78 of the anvil 40. When they contact the anvil 40, the prongs 76 fold around the staple ring 74 to capture the ring and interlock the staples on the anvil side of the plication as shown in FIG. 15B. Rings or other interlocking elements of this type may be used with single- or double-staple row configurations.

Rings 72, 74 are shown as generally circular, although alternative reinforcements of different shapes and patterns may also be used, including those shaped to accommodate linear, oval and other staple patterns.

FIGS. 16a and 16b show two examples of reinforcements 75a, 75b useful for linear staple patterns. As shown, reinforcements are similar to the ring 72 in their use of a plurality of interconnecting members that define openings 73a for receiving staple legs. The legs of any given staple may pass through two laterally positioned openings 73a, longitudinally positioned openings 73a, just a single opening, or any other combination. These reinforcements may be used with linear staplers in a manner described above with respect to the circular staplers. The reinforcements may include members 77 positioned to receive implants that might be used within the body (e.g. pH monitors or other sensors, stimulation/pacing leads, etc.). FIG. 17 illustrates use of the loops 77 to support fasteners 79a, 79b in a system for engaging one tissue plication to another tissue plication. Staples 70 driven through the openings 73a engage the reinforcements and form the plications. The fasteners 79a, 79b are then brought into engagement with one another to draw and couple the plications together. This may be used to form a restriction and/or reduce stomach volume, or for other purposes.

The disclosed reinforcements may be sold as individual components that may be used together with commercially available staplers to reinforce the lines/rings of staples to be delivered by those staplers.

Exemplary Method of Use

One method of using the illustrated system will next be described with reference primarily to FIGS. 8 and 9.

In preparation for use, the orientation of the staple head 42 and the vacuum chamber 18a are adjusted using the appropriate pullwires to place them in their longitudinal positions.

Next, the assembled plicator 10a is passed into the stomach S via the esophagus, preferably through a protective sheath passed through the esophagus. Endoscope 98 is also passed into the stomach to provide visualization of the procedure. The endoscope is preferably mounted to plicator 10a, or it may be a separate component.

The plicator 10a is advanced towards a target location at which a plication is to be formed. The rigidizable cable 86 is manipulated using pull wires to extend vacuum chamber 18a between the fluid lines 58a, 58b and against adjacent stomach tissue. Suction is applied to the vacuum chamber 18 to draw stomach tissue into the vacuum chamber. The gripper arms 90 are closed to pinch the tissue within the chamber, and the vacuum chamber 18a is withdrawn from between the fluid lines 58a, 58b, carrying the engaged tissue with it (see FIG. 4). Consequently, a pocket 100 forms in the tissue such that if the stomach were to be viewed from the outside a depression in the stomach wall would be visible. Serosal tissue surfaces 104 line the outside surfaces of the pocket 100. If gripper arms are not used, suction maintained to stabilize the tissue within the vacuum chamber.

Figure 7A:
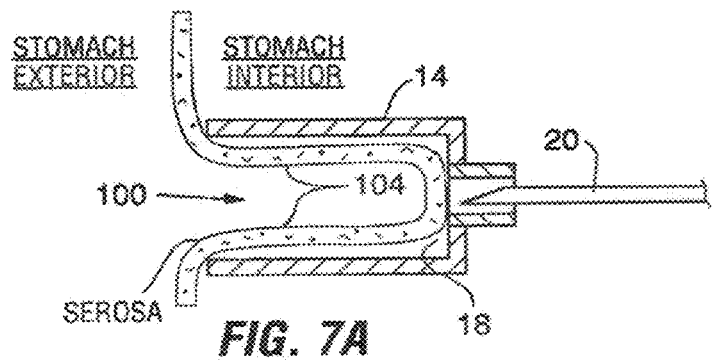
FIGS. 7A through 7E are a sequence of drawings illustrating use of an engaging element to retract tissue that has been engaged by the vacuum head.
Figure 7B:
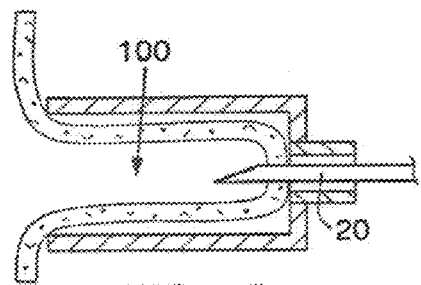
Figure 7C:
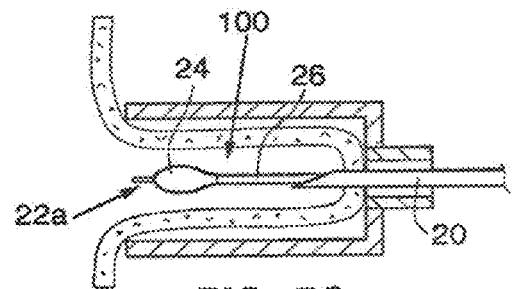
Figure 7D:
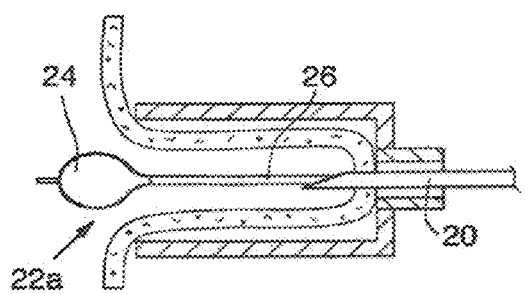
Figure 7E:
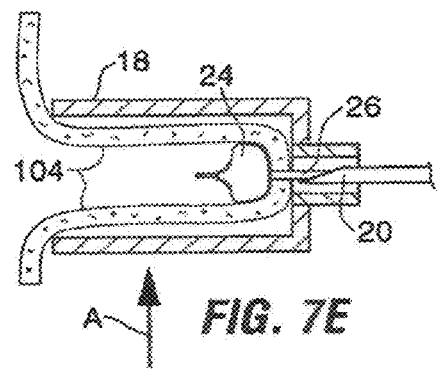

If additional stabilization of the tissue is desired, such as during use of the FIG. 2 embodiment, hollow needle 20 may be advanced through the engaged tissue as shown in FIGS. 7A and 7B, and balloon 24 is inflated within the pocket 100 as shown in FIGS. 7C and 7D. As shown in FIG. 7E, the inflated balloon 24 is withdrawn using catheter 26, thus retracting the tissue surrounding the pocket 100. Alternatively, the engaging element 22b of FIG. 8A, or element 22d of FIGS. 10A and 10B may be deployed and used in similar fashion. If element 22c of FIG. 9 is to be used, the hoop 34 is advanced through the hollow needle 20 into the pocket 100 where it springs to its opened configuration to expand the mesh element 22c.

Figure 13A:
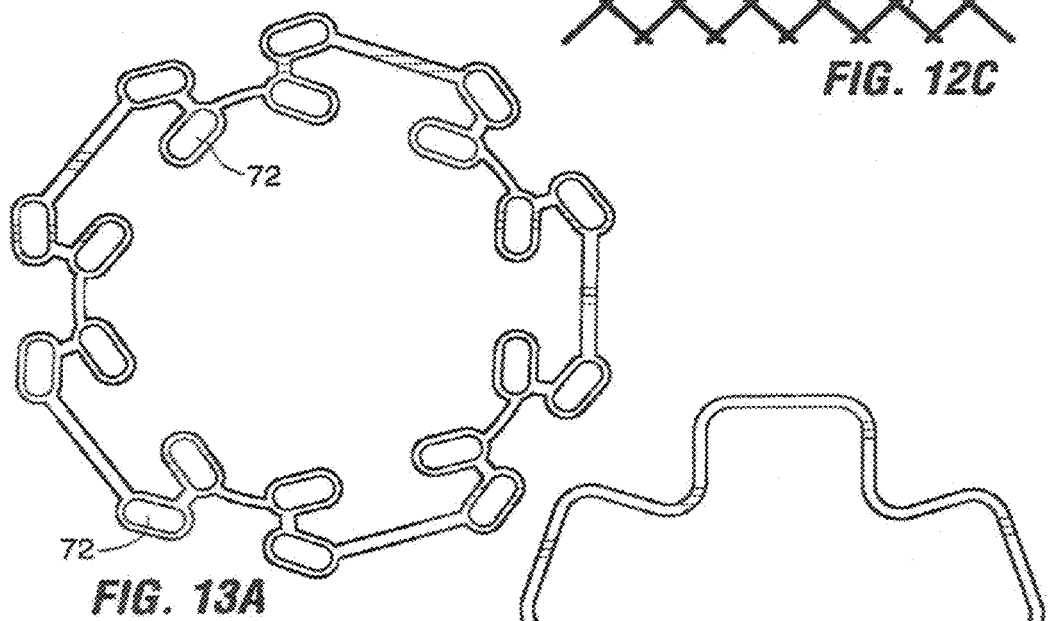
FIGS. 13A and 13B are plan views of reinforcing rings.
Figure 13B:
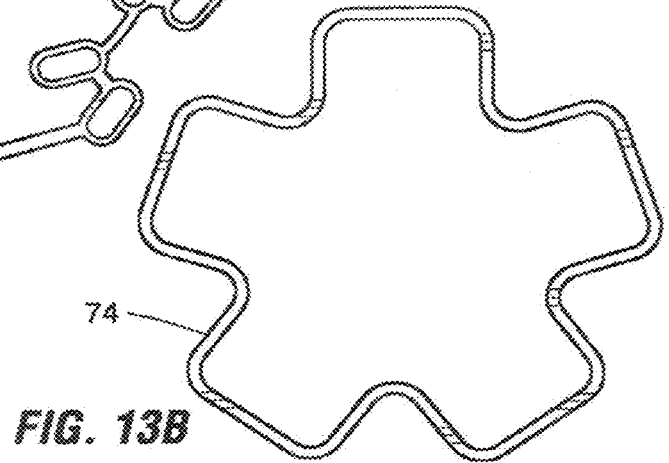

Referring again to FIG. 8, once the tissue has been drawn between the fluid lines 58a, 58b, fluid is driven through fluid line 58a to bring the staple cartridge 44 into contact with the tissue and to compress the tissue between the cartridge 44 and the anvil 40 (see FIG. 4). Once the tissue is fully compressed, fluid pressure is via line 58b, causing the staple driver 46 to advance into contact with staples in the cartridge 44, thus driving the staples through the tissue and simultaneously forming a hole or incision through the layers of stomach wall tissue. The sharp ends of the staples fold against the anvil 40 after passing through the two layers of stomach wall tissue, thus maintaining the plication. If the mucosal reinforcements 72, 74 of FIGS. 13A, 13B are used, the staples engage one or both mucosal reinforcing rings as during stapling.

The procedure may be repeated to form multiple plications if needed. Following formation of the plication(s), a medical implant may be coupled to the hole/incision formed by the hollow needle 20. Coupling may be carried during the course of the same procedure or during a latex procedure scheduled to permit sufficient formation of adhesions between the serosal tissue layers 102 to support the implant.

The system or other components described herein may be packaged with instructions for use instructing a user to utilize the system according to methods disclosed herein.

As is evident from above, the disclosed endoscopic systems function to draw a tissue into the stomach to form a depression on the exterior surface of the stomach, and staple (or suture, or fasten or adhere etc) the opposed stomach wall sections lining the depression together another to form a plication. The system may additionally place material of a type that will promote strong tissue adhesion within the depression (on the exterior of the stomach) and retain the material between the serosal surfaces to enhance. Additionally or alternatively, mucosal reinforcements such as structures that interconnect the staples may be implanted. While these systems provide convenient embodiments for carrying out this function, there are many other widely varying instruments or systems may alternatively be used within the scope of the present invention. Moreover, the disclosed embodiments may be combined with one another in varying ways to produce additional embodiments. Thus, the embodiments described herein should be treated as representative examples of systems useful for forming endoscopic tissue plications, and should not be used to limit the scope of the claimed invention.

Any and all patents, patent applications and printed publications referred to above, including those relied upon for purposes of priority, are incorporated herein by reference.

We claim:

1. A method of stapling tissue within a body cavity, comprising the steps of:
    positioning a stapler within the body cavity, the stapler including a cartridge and an anvil, wherein the cartridge includes staples;
    positioning a staple reinforcement member between the cartridge and the anvil, the staple reinforcement member including a plurality of preformed openings connected by elongated struts;
    positioning tissue between the cartridge and the anvil; and
    driving staples from the cartridge through the tissue positioned between the cartridge and the anvil.

2. The method of claim 1, wherein driving the staples from the cartridge includes driving a staple driver into the cartridge using fluid pressure.

3. The method of claim 1, wherein positioning tissue between the cartridge and the anvil includes applying suction to the tissue.

4. The method of claim 3, wherein applying suction includes positioning an opening of a vacuum chamber against the tissue.

5. The method of claim 3, wherein the suction is applied to the tissue by positioning a vacuum chamber located between the cartridge and the anvil and coupled to a source of negative pressure against the tissue to draw the tissue into a space between the cartridge and the anvil.

6. The method of claim 5, wherein driving the staples includes driving a circular array of staples through the tissue positioned between the cartridge and the anvil.

7. The method of claim 1, wherein driving the staples forms a fold of stapled tissue.

8. The method of claim 1, wherein driving the staples includes driving the staples through the tissue reinforcing member, causing the staples to engage the tissue reinforcing member.

9. The method of claim 1, wherein each of the preformed openings receives only a single leg of only one staple.

10. The method of claim 1, wherein positioning the staple reinforcement member includes positioning the staple reinforcement member adjacent to the cartridge prior to driving the staples.

11. The method of claim 1, further including advancing at least one of the anvil or the cartridge to compress the tissue positioned between the cartridge and the anvil prior to driving the staples.

12. The method of claim 1, further including forming a cut through the tissue positioned between the cartridge and the anvil using a cutting element other than a staple.

13. The method of claim 12, wherein forming the cut includes forming a cutout through the tissue, and wherein the staples encircle the cutout.

14. The method of claim 1, wherein a distal portion of the shaft includes a first branch having the cartridge and anvil thereon and a second branch having an engaging instrument thereon, and wherein the second branch is coupled to a vacuum chamber used to position the tissue between the cartridge and anvil.

15. The method of claim 1, wherein the staples are arranged in a circular pattern with approximately equidistant space between all adjacent staples.

16. A stapling system, comprising:
    a stapler head including a cartridge containing staples and an anvil spaced apart from the cartridge along an axis, wherein the staples are arranged in a circular pattern that extends around the axis; and
    a staple reinforcement ring positioned between the cartridge and the anvil and defining a plurality of preformed openings connected by elongated struts.

17. The stapling system according to claim 16, wherein the staple reinforcement member is configured to link the legs of at least some of the staples after the staples are released from the cartridge.

18. The stapling system according to claim 16, further comprising a vacuum chamber fluidly coupled to a source of negative pressure.

19. The stapling system according to claim 16, wherein at least one of the anvil or the cartridge is configured to advance along the axis to compress the tissue positioned between the cartridge and the anvil.

20. The stapling system according to claim 16, wherein the reinforcing ring is positioned adjacent the cartridge.

21. The stapling system according to claim 16, further including a cutting element operatively associated with the stapler head to form a cut through tissue during stapling using staples in the cartridge.

22. The stapling system according to claim 21, wherein the cutting element is a punch shaped to punch a hole through the tissue.

23. The stapling system according to claim 21, wherein the cutting element is positioned such that the cut is formed to be surrounded by staples.

24. The stapling system according to claim 16, further including a piston coupled to a staple driver, a chamber housing the piston, and a fluid source fluidly coupled to the housing, the staple driver positioned such that directing fluid from the fluid source into the chamber advances the staple driver to the staple cartridge.

25. The stapling system according to claim 16, wherein the axis passes through the cartridge and the anvil, and wherein at least one of the cartridge or the anvil is configured to move towards the other of the cartridge or the anvil parallel to the axis.

26. The stapling system according to claim 16, further including a piston coupled to the cartridge, a chamber housing the piston, and a fluid source fluidly coupled to the housing, the cartridge positioned such that directing fluid from the fluid source into the chamber advances the cartridge towards the anvil for tissue compression.

27. The stapling system according to claim 16, wherein the cartridge and the anvil are pivotally coupled to a distal end of the elongated shaft.

28. A method of reinforcing an array of staples delivered to tissue through a stapler, the method comprising:
    providing a staple reinforcement member defining a plurality of preformed openings for receiving legs of the staples when the array of staples is delivered to the tissue, wherein each leg corresponds to a single preformed opening, and each preformed opening corresponds to a single leg;
    positioning the staple reinforcement member between an anvil and a cartridge of the stapler;
    positioning body tissue between the cartridge and the anvil; and driving a plurality of staples from the cartridge, causing each leg of the staples to pass through the corresponding single preformed opening of the staple reinforcement member.

29. The method of claim 28, wherein the staple reinforcement member is ring shaped and the plurality of preformed openings are arranged in a circular pattern around a central opening.

30. The method of claim 29, wherein the staple reinforcement member is configured to link the legs of at least some of the staples after the staples are driven from the cartridge.

31. The method of claim 30, wherein the plurality of preformed openings are connected by elongated struts.

32. The method of claim 30, wherein a number of openings of the plurality of preformed openings is such that no preformed opening is without a staple leg after the staples are driven from the cartridge.

* * * * *